(12) United States Patent
Lee et al.

(10) Patent No.: US 7,731,665 B2
(45) Date of Patent: Jun. 8, 2010

(54) APPARATUS AND METHOD FOR MEASURING BIOLOGICAL INFORMATION

(75) Inventors: Kwy-Ro Lee, Seoul (KR); Hyun-Ho Oh, Seoul (KR); Min-Jae Jung, Seoul (KR); Hyung-Ki Hong, Gyeonggi-Do (KR); Seong-Moon Cho, Gyeonggi-Do (KR); Youn-Jae Lee, Seoul (KR)

(73) Assignee: LG Electronics, Inc., Seoul (KR)

( * ) Notice: Subject to any disclaimer, the term of this patent is extended or adjusted under 35 U.S.C. 154(b) by 0 days.

(21) Appl. No.: 11/470,227

(22) Filed: Sep. 5, 2006

(65) Prior Publication Data

US 2007/0078310 A1    Apr. 5, 2007

(30) Foreign Application Priority Data

Sep. 7, 2005    (KR) .................. 10-2005-0083217
May 2, 2006    (KR) .................. 10-2006-0039675

(51) Int. Cl.
*A61B 5/02* (2006.01)

(52) U.S. Cl. .................. 600/501; 600/310; 600/324; 600/473; 600/476; 600/502

(58) Field of Classification Search .............. 600/310, 600/323, 324, 473, 476, 500, 501, 502
See application file for complete search history.

(56) References Cited

U.S. PATENT DOCUMENTS

| | | | | |
|---|---|---|---|---|
| 4,800,885 A | * | 1/1989 | Johnson | 600/330 |
| 4,848,901 A | * | 7/1989 | Hood, Jr. | 356/41 |
| 5,515,847 A | * | 5/1996 | Braig et al. | 600/316 |
| 5,941,837 A | * | 8/1999 | Amano et al. | 600/595 |
| 6,595,929 B2 | * | 7/2003 | Stivoric et al. | 600/549 |
| 6,985,767 B2 | * | 1/2006 | Horiuchi et al. | 600/476 |
| 7,445,600 B1 | * | 11/2008 | Carr et al. | 600/490 |
| 2005/0124871 A1 | * | 6/2005 | Baker et al. | 600/323 |
| 2006/0183988 A1 | * | 8/2006 | Baker et al. | 600/336 |

* cited by examiner

*Primary Examiner*—Long V Le
*Assistant Examiner*—Ellsworth Weatherby
(74) *Attorney, Agent, or Firm*—Lee, Hong, Degerman, Kang & Waimey

(57) ABSTRACT

An apparatus and method for precisely measuring various biological information of a user's body by using a single measuring apparatus enable precisely and effectively measuring biological information including body fat, pulse and a blood vessel aging degree. By measuring an infrared absorbance or infrared rays irradiated to a measurement target according to a modulation and tuning method and obtaining the information with reference to supplementary biological information obtained from a user, the plurality of biological information can be precisely measured at a low driving voltage through the modulation and tuning method by using a single infrared light source. Also, the measuring apparatus can be reduced in size by simplifying its construction and can be effectively integrated into various device.

25 Claims, 17 Drawing Sheets

APPARATUS AND METHOD FOR MEASURING BIOLOGICAL INFORMATION

CLAIM FOR PRIORITY

This application is based on and claims priority to Korean Patent Application Nos. 2005-0083217 filed on Sep. 7, 2005 and 2006-0039675 filed on May 2, 2006 in the Korean Intellectual Property Office (KIPO), the entire contents of which are hereby incorporated by reference.

BACKGROUND OF THE INVENTION

1. Field of the Invention

The present invention relates to an apparatus and method for measuring biological information and, more particularly, to an apparatus and method for precisely measuring various biological information by using a single measuring apparatus.

2. Description of the Related Art

As the people are becoming more interested in their health, many devices have been developed to allow users to obtain basic information related to various biological measurements through a simple operation at home. For example, mobile diagnosing devices have been developed and actively used to allow user to simply measure values of body fat, pulse, blood pressure, blood sugar, etc. at home without having to see a doctor.

The body mass index (BMI) denotes an amount of fat within a human body and is used as a major index for determining obesity. Among methods for measuring the body fat, a bio-electrical impedance measuring method and a near-infrared ray interactance optical method use a device.

The bioelectrical impedance measuring method measures the electrical impedance of the human body by applying a small current to the human body. That is, in this method, a ratio of the lean and fat body compositions is measured by using the characteristics that lean and fat compositions of the body have a different electrical resistance value.

In the near-infrared interactance optical method, by using the characteristics that lean and fat compositions of the body each absorbs light of a specific wavelength of a near infrared red region, the amount of light absorption that each composition absorbs or a transmission amount of light is measured and accordingly a ratio of the body compositions is calculated.

The bioelectrical impedance method had been developed a long time ago and frequently used traditionally with high precision, but because it is expensive and its measurement time is long, recently, the near-infrared interactance optical method which is relatively low-priced with short measurement time is increasingly used.

Although the precision of the near-infrared interactance optical method is inferior and a standardization operation must be performed before measurement, a measurement device of the optical method has been improved to have similar precision to that of the bioelectrical impedance method in line with the development of the optical technologies.

In the near-infrared interactance optical method, an absorption amount of infrared rays of each wavelength is relatively compared by using a plurality of infrared wavelengths according to each wavelength where an infrared absorption peak of each body composition appears. And it is compared with a measurement value of a standard test sample to show a ratio of each body composition.

However, the absorption peaks of each body composition, for example, an absorption peak of fat is 930 nm, moisture is 970 nm, and protein is 910 nm and 1020 nm, etc. are quite similar. In this respect, it is very difficult to fabricate an infrared light source such that infrared rays of a wavelength corresponding to their current peak positions are accurately radiated and bandwidths do not overlap.

In addition, because the plurality of infrared wavelengths are used, a signal processing circuit is complicated and a size and cost of a product increase.

FIG. 1 is a graph showing absorption of each wavelength of infrared radiation and FIG. 2 is a graph showing a relationship between the infrared absorbance and the body fat.

With reference to FIGS. 1 and 2, it is noted that an absorption amount of oil is smaller than that of other material over the full wavelength band (refer to FIG. 1). For a person with more muscle (comprising water by more than 70%) and less fat, infrared rays can hardy transmit therethrough, and for a person with less muscle and more fat, infrared rays can easily transmit therethrough.

Accordingly, by using a sample of a body whose body fat is known, a relationship between the body fat and the infrared absorbance can be obtained and expressed by the equation shown below (refer to FIG. 2):

$$\text{Body fat}=K_0+K_1(\log 1/l)+K_2(W/100)+K_3(H/100)+K_4(S)+K_5(EL)$$

wherein $K_0$, $K_1$, $K_2$, $K_3$, $K_4$ and $K_5$ respectively indicate proportional constants, 'I' indicates the infrared absorbance, 'W' indicates weight, 'H' indicates height, 'S' indicates gender and 'EL' indicates an exercise level.

The above equation also shows that the body fat has a relationship with the age, weight, height, gender and quantity of motion in addition to the infrared absorbance, and a ratio of body fat can be reversely calculated by measuring the infrared absorbance based on the formula.

There have been developed several methods for measuring the pulse (heart rate) of the human body, and among them, the optical method using the near infrared rays is the most suitable in consideration of user convenience, cost and portability. The principle of measuring pulse by the optical method will now be described with reference to FIG. 3.

FIG. 3 is a graph showing a change in the infrared absorbance according to each pulse period. As shown, when the amount of component of blood in a capillary that is periodically changed according to the heart rate by using the blood component of a blood vessel and an absorption spectrum of the infrared light of a particular wavelength is measured, the infrared absorbance also periodically changes, so the pulse can be measured by counting the period.

In addition, a degree of elasticity and aging of the blood vessel can be recognized by using the signals obtained by optically measuring the pulse signal.

The measured pulse signal as shown in FIG. 3 is differentiated to obtain a signal as shown in FIG. 4A, which is called an accelerated plethymogram signal.

Each peak of the accelerated plethymogram signal has meaningful information regarding a blood vessel and the heart. Accordingly, by scoring the size of each peak and waveforms by using a certain formula, and classifying the scores by stages, elasticity and aging state of the blood vessel can be known according to a shape of the accelerated plethymogram signal.

The formula used for classifying by stages can be expressed as follows:

$$\text{Score}=(-b+c+d)/a$$

(a, b, c, d=size of each peak of the accelerated plethymogram signal).

The waveforms classified into A to G by scoring according to the formula are as shown in FIG. 4B.

However, in case of the optical body fat measurement device, the optical pulse measurement device and a blood vessel elasticity measurement device using the same, although they use the infrared rays, because they use mutually different infrared wavelengths, it is difficult to implement both the body fat and pulse measurement function and the blood vessel elasticity measurement function in a single device.

BRIEF DESCRIPTION OF THE INVENTION

Therefore, it is a first object of the present invention to provide an apparatus and method for measuring biological information which are capable of measuring body fat, pulse and blood vessel elasticity as a single apparatus by using infrared radiation with a single wavelength of a certain range.

It is a second object of the present invention to provide an apparatus and method for measuring biological information which are capable of simplifying the construction and processing method thereof by measuring a plurality of biological information by using infrared radiation with a single wavelength, so as to be easily applied for various mobile devices.

It is a third object of the present invention to provide an apparatus and method for measuring biological information which are capable of improving a signal-to-noise ratio to thus increase measurement precision by processing infrared ray transmission signals and signals of an infrared receiving unit according to a modulation and demodulation method and by applying a matching filter for demodulation.

It is a fourth object of the present invention to provide an apparatus and method for measuring biological information which are capable of reducing the necessary strength of light of a near infrared light emitting unit to thus reduce power consumption by modulating a signal of the light emitting unit for measurement of biological information and providing the signal, and by demodulating a signal received by a near infrared light receiving unit to suppress an introduction of noise.

It is a fifth object of the present invention to provide an apparatus and method for measuring biological information which are capable of obtaining a high signal-to-noise ratio although a size of a measurement signal is small by removing a DC offset and an RF external light noise by tuning and filtering a signal that has received modulated near infrared light and performing a band pass filtering on the signal.

It is a sixth object of the present invention to provide an apparatus and method for measuring biological information which are capable of simplifying the construction of an analog circuit by operating at least one of a unit for receiving modulated near infrared light and tuning and amplifying it and a unit for matching and filtering the tuned and amplified signal in a digital manner through a digital signal processing unit.

It is a seventh object of the present invention to provide an apparatus and method for measuring biological information which are capable of flexibly controlling characteristics of tuning-amplifying and matching/filtering so as to be applicable for measuring various biological signals by operating at least one of a unit for receiving modulated near infrared light and tuning and amplifying it and a unit for matching and filtering the tuned and amplified signal through a digital signal processing unit.

It is an eighth object of the present invention to provide an apparatus and method for measuring biological information which are capable of being applied for various applications without a burden so as to add various biological signal measurement functions and thus remarkably improve utilization of an applied application, by reducing luminous element driving power for measurement and an amplification degree for a noise cancellation of a measured value.

To achieve these and other advantages and in accordance with the purposes of the present invention, as embodied and broadly described herein, there is provided an apparatus for measuring biological information including: an input unit for selecting one of a body fat measurement mode, a pulse measurement mode and a blood vessel aging degree measurement mode; a memory storing user biological information; infrared ray transmission/reception units for irradiating infrared rays with a single wavelength of a certain range, and measuring an infrared absorbance of a certain portion of a human body by analyzing a reflected amount of the irradiated infrared rays; a controller for calculating at least one of a body fat value, a pulse value and a blood vessel aging degree value by using the measured infrared absorbance and biological information according to the measurement mode selected by the input unit; and a display unit for displaying at least one of the calculated body fat value, the pulse value and the blood vessel aging degree value.

To achieve the above objects, there is also provided a method for measuring biological information including: selecting one of a body fat measurement mode, a pulse measurement mode and a blood vessel aging degree measurement mode, irradiating infrared rays with a single wavelength of a certain range to a particular portion of a human body, and measuring an infrared absorbance of the human body by analyzing a reflected amount of the irradiated infrared rays; calculating at least one of a body fat value, a pulse value and a blood vessel aging degree value by using the measured infrared absorbance and pre-set user biological information according to the selected measurement mode; and displaying at least one of the calculated body fat value, the pulse value and the blood vessel aging degree value.

To achieve the above objects, there is also provided an apparatus for measuring biological information including: a light emitting unit for operating a luminous element with a modulated signal; a light receiving unit for receiving light from the luminous element of the light emitting unit and providing a measurement voltage; a tuning unit for tuning a signal of the light receiving unit to cancel a DC noise and an RF noise; a matching unit for demodulating a signal of the tuning unit to cancel a harmonic noise; and a measurement controller for providing a corresponding biological signal measurement result based on an output of the matching unit.

To achieve the above objects, there is also provided a method for measuring biological information including: illuminating a light source based on a modulation signal; receiving light according to the light source and canceling noise therein; demodulating the noise-canceled signal and removing a harmonic wave; and calculating a corresponding biological signal measurement result based on the harmonic wave noise-canceled signal.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE INVENTION

Figure 1:
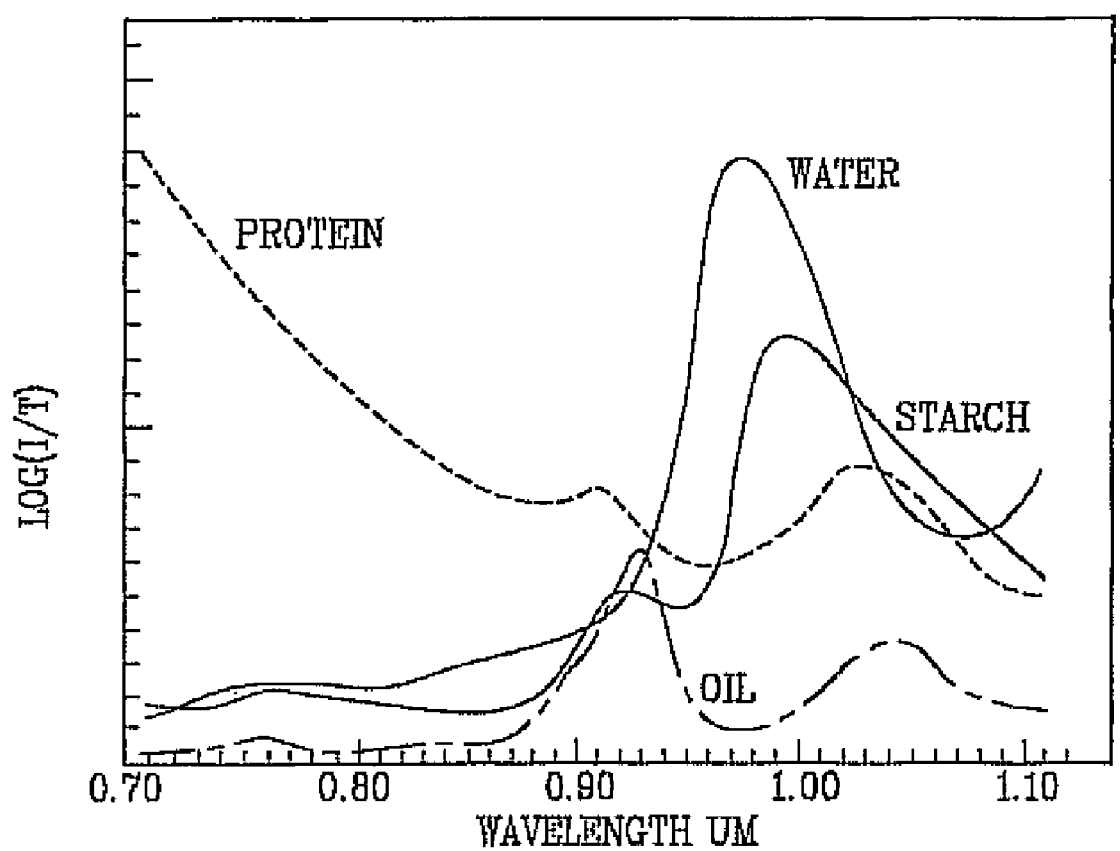
FIG. 1 is a graph showing absorption of infrared radiation by wavelength.
Figure 2:
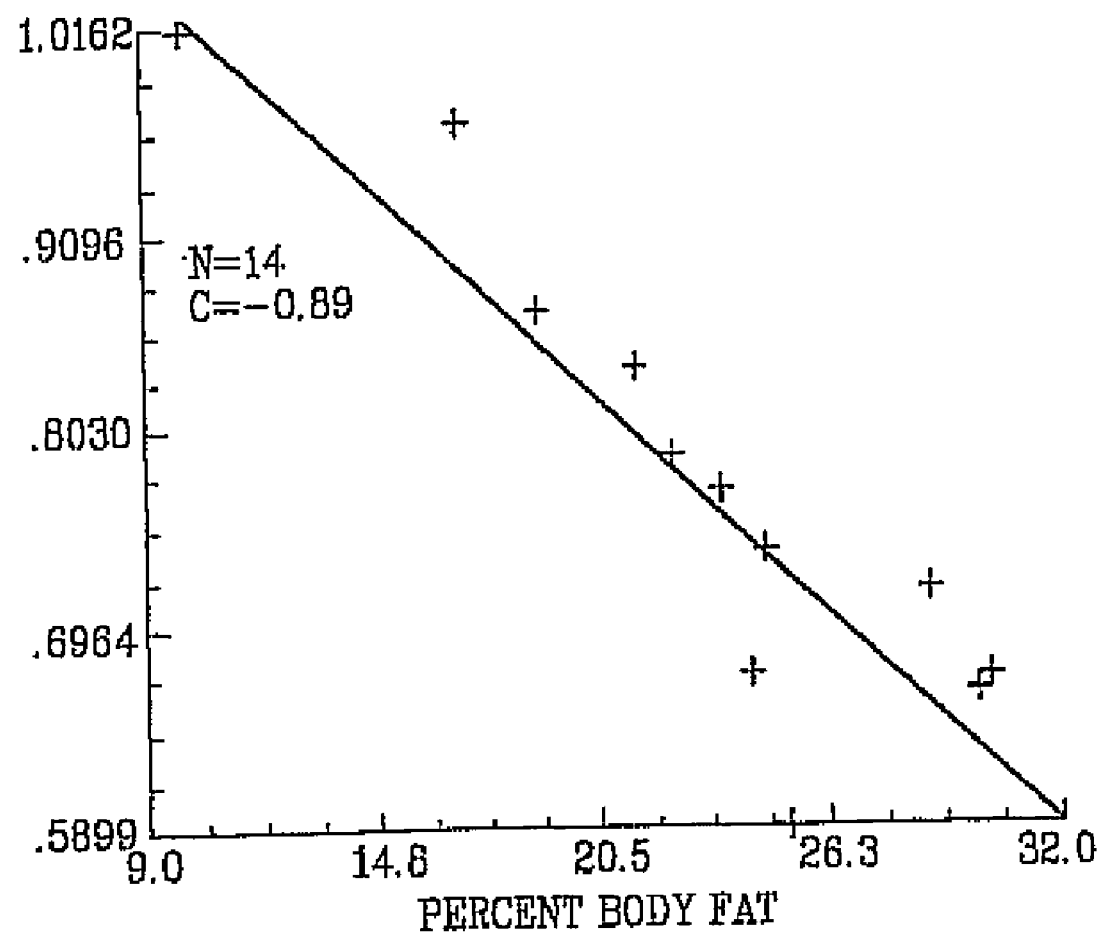
FIG. 2 is a graph showing a relationship between an infrared absorbance and body fat.
Figure 3:
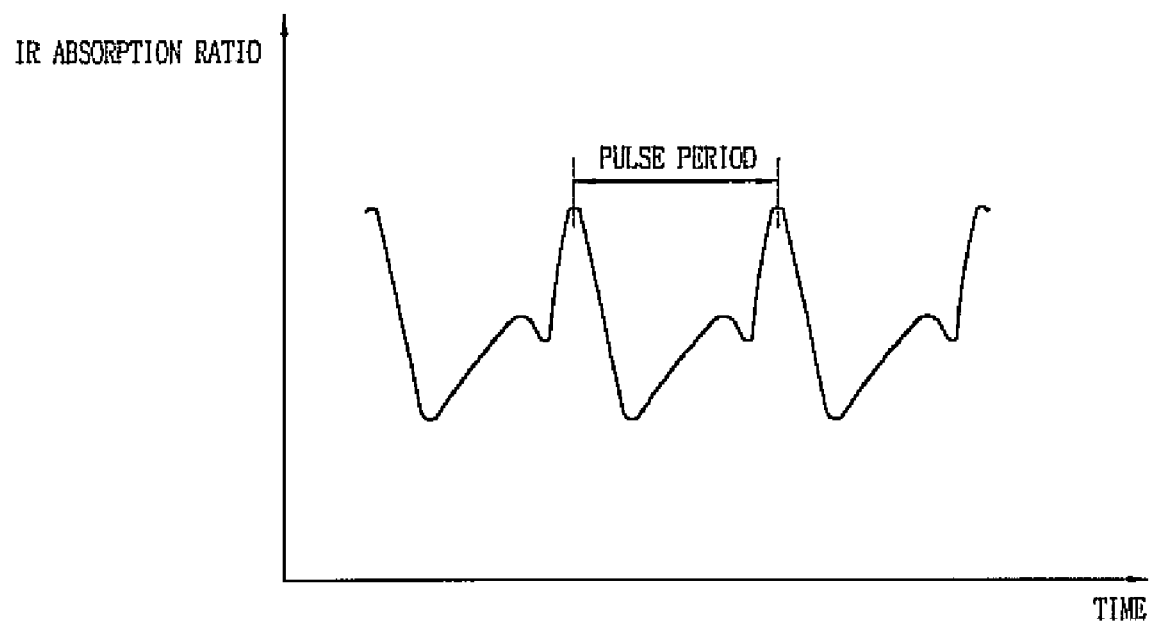
FIG. 3 is a graph showing a change in the infrared absorbance according to a pulse period.
Figure 4A:
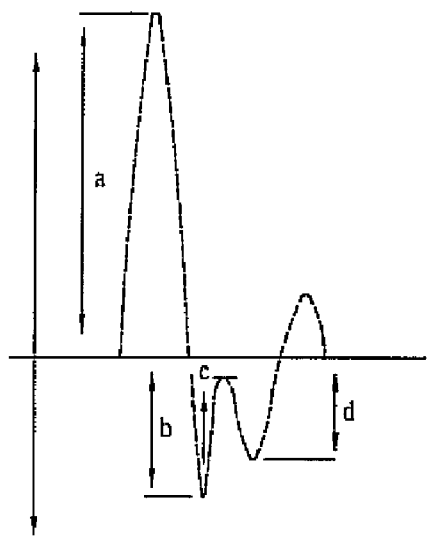
FIG. 4A is a graph showing a pulse signal that is secondarily differentiated over time.
Figure 4B:
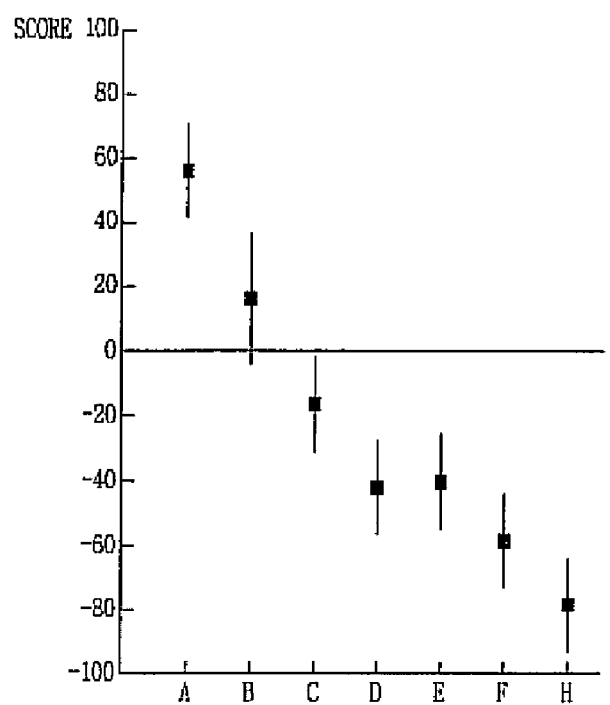
FIG. 4B is a graph showing a size of each peak and a waveform of an accelerated plethymogram signal that are scored and classified.
Figure 5:
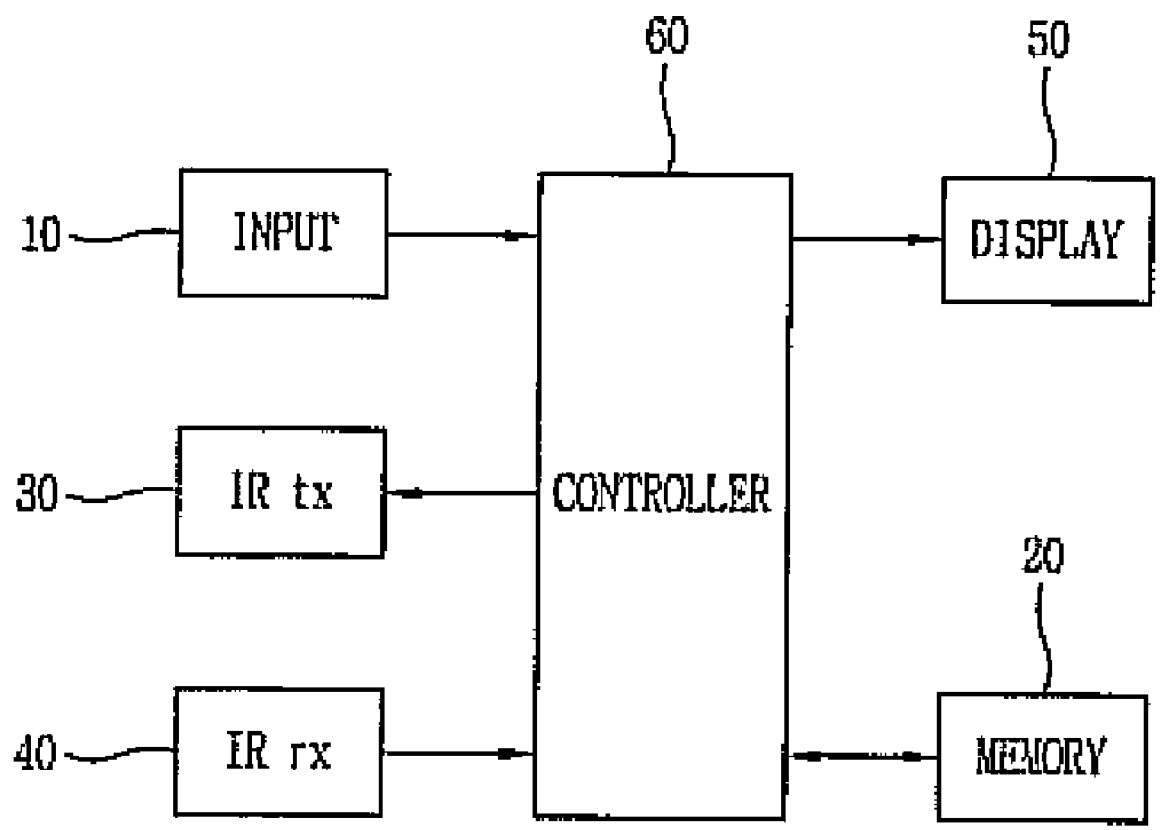
FIG. 5 is a schematic block diagram of the construction of an apparatus according to a first embodiment of the present invention.

FIG. 5 is a schematic block diagram illustrating the construction of an apparatus according to a first embodiment of the present invention. As shown in FIG. 5, an input unit 10 includes a plurality of user-manipulatable keys or buttons (not shown) and outputs key signals with respect to the user-manipulated keys to a controller 60 to cause the controller 60 to perform a corresponding operation.

Preferably, a user manipulates the input unit 10 to output a key signal for selecting one of a body fat measurement mode for measuring body fat, a pulse measurement mode for measuring pulse, and a blood vessel aging degree measurement mode for measuring a blood vessel aging degree to the controller 60.

A memory 20 stores biological information such as age, weight, height, gender and an amount of exercise of the user. The biological information can be stored in the memory 20 by the user through manipulation of the input unit 10.

An infrared ray transmission unit 30 irradiates infrared rays with a single wavelength of a certain range to a particular portion of the user's body. The wavelength of the infrared rays has a range of 700 nm to 1,000 nm, and preferably, the infrared ray transmission unit 30 irradiates the infrared ray with a wavelength of 940 nm. Namely, when the body fat measurement mode or the pulse measurement mode is activated, the infrared ray with the wavelength of 940 nm are irradiated onto the particular portion of the user's body desired to be measured. The infrared ray transmission unit 30 may include at least one or more infrared light emitting diodes (LEDs).

An infrared ray receiving unit 40 analyzes a reflection amount of the infrared rays irradiated by the infrared ray transmission unit 30 to measure an infrared absorbance of the particular portion of the user's body, and outputs the infrared absorbance measurement value to the controller 60. Preferably, the infrared ray receiving unit 40 is formed as an infrared photodiode or an infrared photo-transistor. More preferably, at least one or more of the infrared LEDs comprising the infrared ray transmission unit 30 are arranged centering around the infrared photodiode or the infrared photo-transistor.

A display unit 50 receives display data with respect to the key signals inputted from the input unit 10 and displays it under the control of the controller 60, and displays at least one of the calculated body fat value, the pulse value and the blood vessel aging degree value according to the present invention.

The controller 60 controls the general operation of the biological information measuring apparatus.

Figure 6:
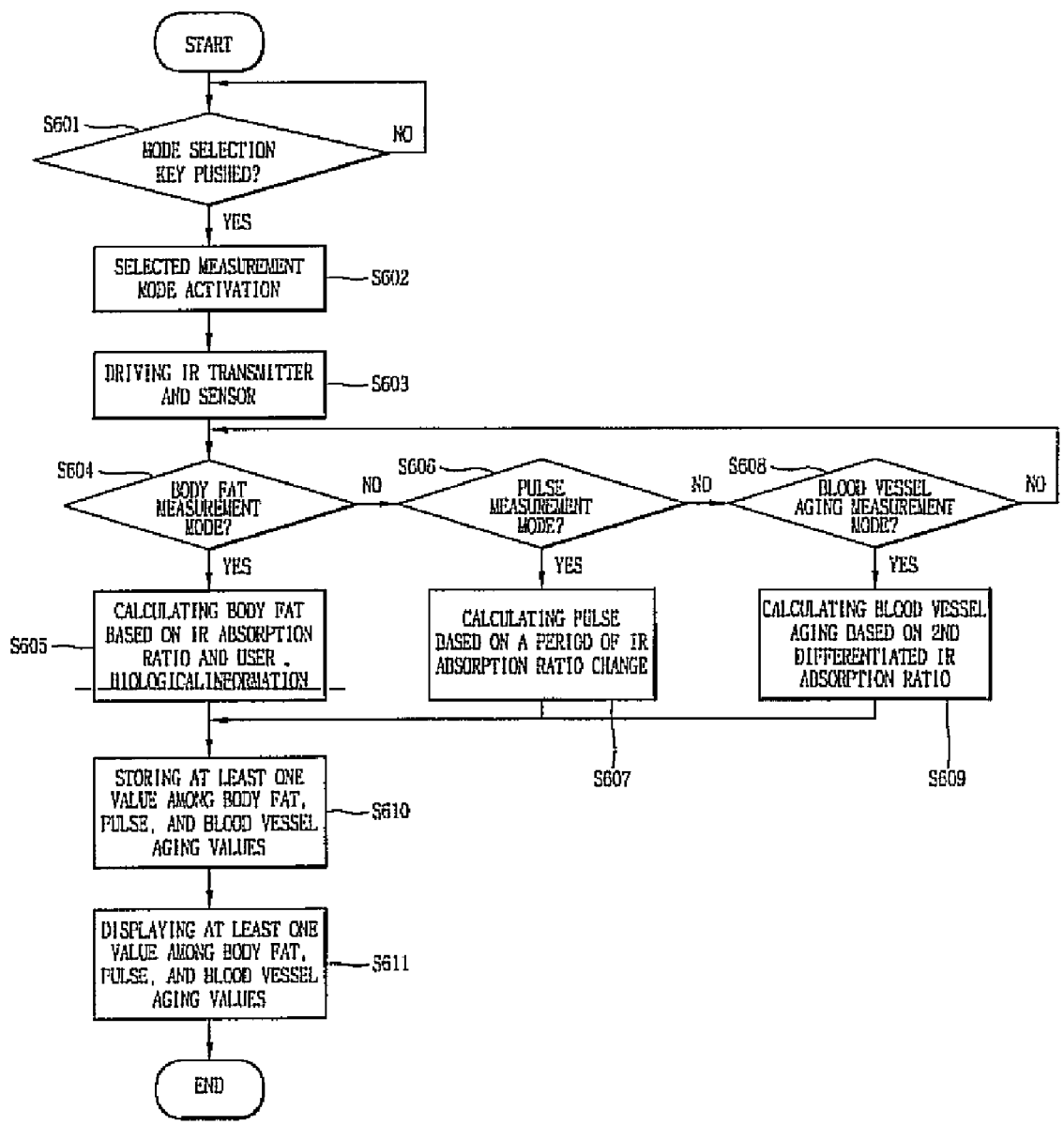
FIG. 6 is a flow chart of an operation of a method according to the first embodiment of the present invention.

FIG. 6 is a flow chart illustrating the processes of a method for measuring biological information of the biological information measuring apparatus according to the first embodiment of the present invention.

First, when the controller of the biological information measuring apparatus receives a key signal for selecting one of the body fat measurement mode, the pulse measurement mode and the blood vessel aging degree measurement mode through the input unit 10 (step S601), it activates a measurement mode corresponding to the inputted select key signal (step S602) and drives the infrared ray transmission unit 30 and the infrared ray receiving unit 40 (step S603). At this time, the infrared ray transmission unit 30 irradiates infrared rays of a single wavelength of a certain range to a particular portion of the user's body desired to be measured. The wavelength of the infrared rays has a range of 700 nm to 1,000 nm, and preferably, a near-infrared wavelength of 940 nm is used.

The infrared ray receiving unit 40 analyzes a reflection amount of the infrared rays irradiated by the infrared ray transmission unit 30 to measure an infrared absorbance of the particular portion of the user's body and outputs the infrared absorbance measurement value to the controller 60.

When the measurement mode selected by the user in the step S601 is the body fat measurement mode (step S604), the controller 60 calculates a body fat value by using the infrared absorbance measurement value inputted through the infrared ray receiving unit 40 and the biological information of the user previously stored in the memory 20 (step S605).

When the measurement mode selected by the user in the step S601 is the pulse measurement mode (step S606), the controller 60 calculates a pulse value by analyzing a period of a change amount of the infrared absorbance measurement value inputted through the infrared ray receiving unit 40 (step S607).

When the measurement mode selected by the user in the step S601 is the blood vessel aging degree measurement mode (step S608), the controller 60 secondarily differentiates a change in the infrared absorbance measurement value inputted through the infrared ray receiving unit 40 over time and calculates and analyzes a score to obtain a blood vessel aging degree value (step S609).

Thereafter, the controller 60 stores at least one of the body fat value, the pulse value an the blood vessel aging degree value calculated in the step S604 or in the step S609 in the memory 20 according to a user setting (step S610).

And the controller 60 displays at least one of the body fat value, the pulse value an the blood vessel aging degree value calculated in the step S604 or in the step S609 in the memory 20 according to a user setting (step S611).

Figure 7:
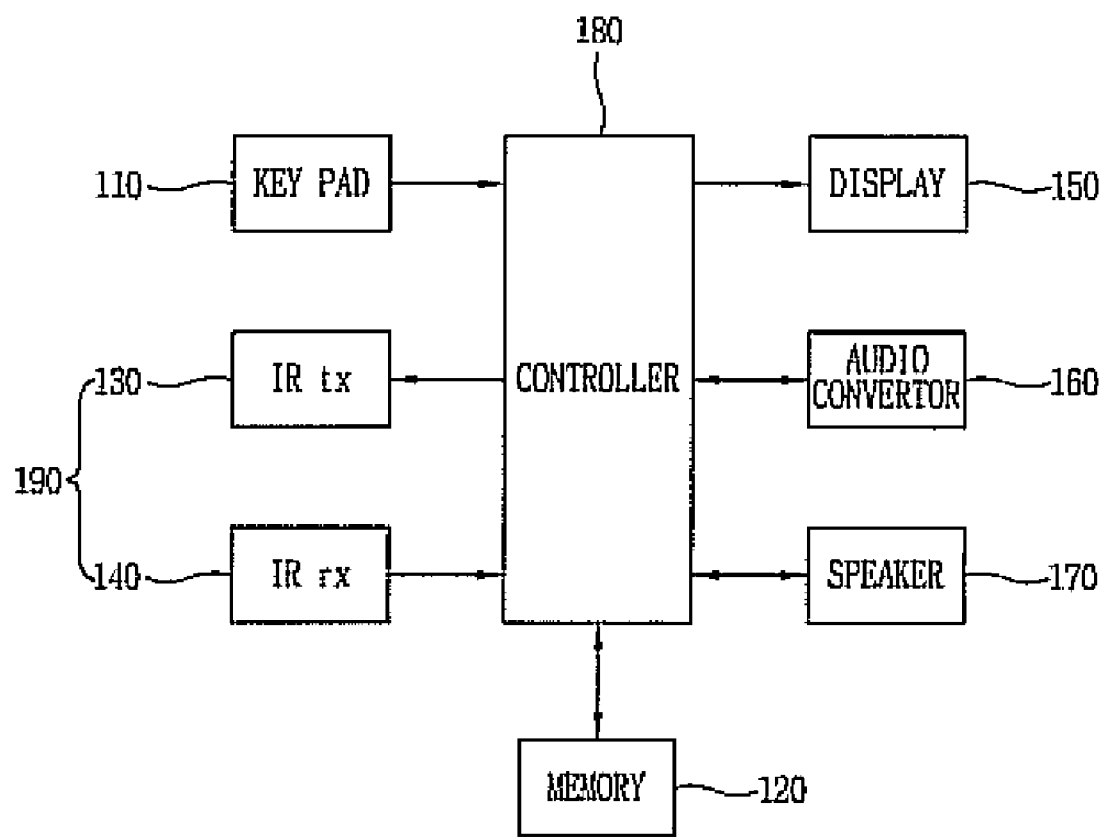
FIG. 7 is a schematic block diagram of the construction of an apparatus according to a second embodiment of the present invention applied to a mobile terminal.

FIG. 7 is a schematic block diagram illustrating the construction of a mobile terminal having a biological information function according to a second embodiment of the present invention. A particular functional part can be physically shared by combining the construction of the apparatus of FIG. 5 with the construction of the mobile terminal, to reduce an actually added physical functional part. This means that adding of the construction of the apparatus of FIG. 5 will not increase a cost or volume.

First, a keypad 110 includes a plurality of number keys and functional keys and outputs key signals with respect to the keys manipulated by a user to a controller 180 to cause the controller 180 to perform a corresponding operation. The keypad 110 can output a key signal for selecting one of a body fat measurement mode for measuring body fat, a pulse measurement mode for measuring pulse, and a blood vessel aging degree measurement mode for measuring a blood vessel aging degree upon manipulation by a user and various biological information inputted by the user, and provide it to the controller 180.

A memory 120 stores a certain program for controlling a general operation of the mobile terminal and biological information such as age, weight, height, gender and an amount of exercise of the user, The biological information can be stored in the memory 120 by the user through various input methods.

An infrared ray transmission unit 130 and an infrared ray receiving unit 140 have the same structure as that shown in FIG. 5, and because they are physically arranged to be adjacent, they can be comprised as an infrared ray sensor unit 190.

A display unit 150 receives display data with respect to the key signals inputted from the keypad 110 and displays it according to a control signal from the controller 180, and also displays an operation state of the mobile terminal and a plurality of information in the form of icons and characters. In addition, according to the present embodiment of the present invention, the display unit 150 displays at least one of the body fat value, the pulse value and the blood vessel aging degree value calculated by the controller 180.

A voice conversion unit 160 converts at least one of the body fat value, the pulse value and the blood vessel aging degree value calculated by the controller 180 into a voice signal and outputs the converted voice signal to a speaker 170. The voice conversion unit 160 is not an essential element and can be added in terms of utilization of an established functional part of the mobile terminal.

The controller 180 performs control of the functions according to the present embodiment of the present invention as well as a general control to perform the functions of the mobile terminal.

Figure 8A:
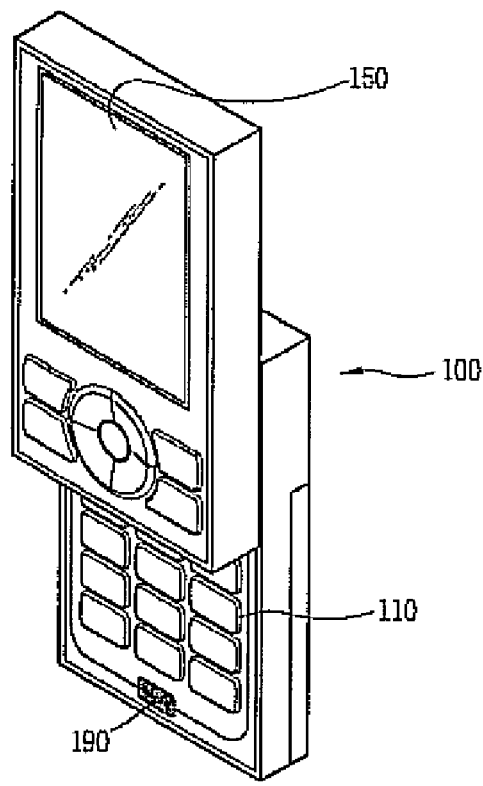
FIGS. 8A and 8B are exemplary views of an application of the apparatus of FIG. 7 to a mobile terminal.
Figure 8B:
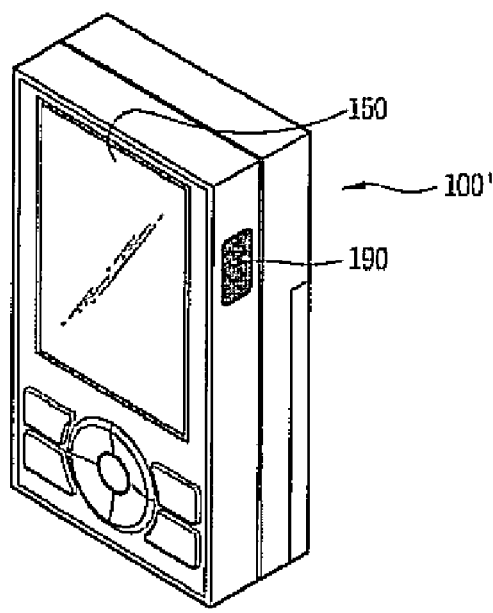

FIGS. 8A and 8B are exemplary views of applications of the mobile terminal of FIG. 7. FIG. 8A shows that the infrared ray sensor unit 190 is disposed near the keypad 110 of a slide type mobile terminal 100 and a required circuit is applied to the interior of the terminal 100. FIG. 8B shows that the infrared ray sensor unit 190 is disposed at a portion of the side of the slide type terminal 100' and a required circuit is applied to the interior of the terminal 100'. As a matter of course, the infrared ray sensor unit 190 can be disposed at a proper position of the terminal according to the structure of the terminal. Accordingly, not only simple biological information can be measured but also a biological signal of the user can be measured during call communication by using a storing user interface of the mobile terminal, a calculation function and a display function, a health state of the user can be automatically checked by measuring the biological signal of the user when the user carried around the mobile terminal, or a service (e.g., an advice service based on the health state, a service for providing composed music or an appropriate voice when the user's pulse becomes rapid, etc.) can be provided by using the biological signal of the user in association with various supplementary functions.

In addition, because the mobile terminal typically includes a controller having one or more digital signal processing functions of high performance, the biological signal measurement means can be implemented through the existing controller without the necessity of any other separate controller and its operation can be performed. Accordingly, various biological signals can be precisely measured at a low cost.

Figure 9:
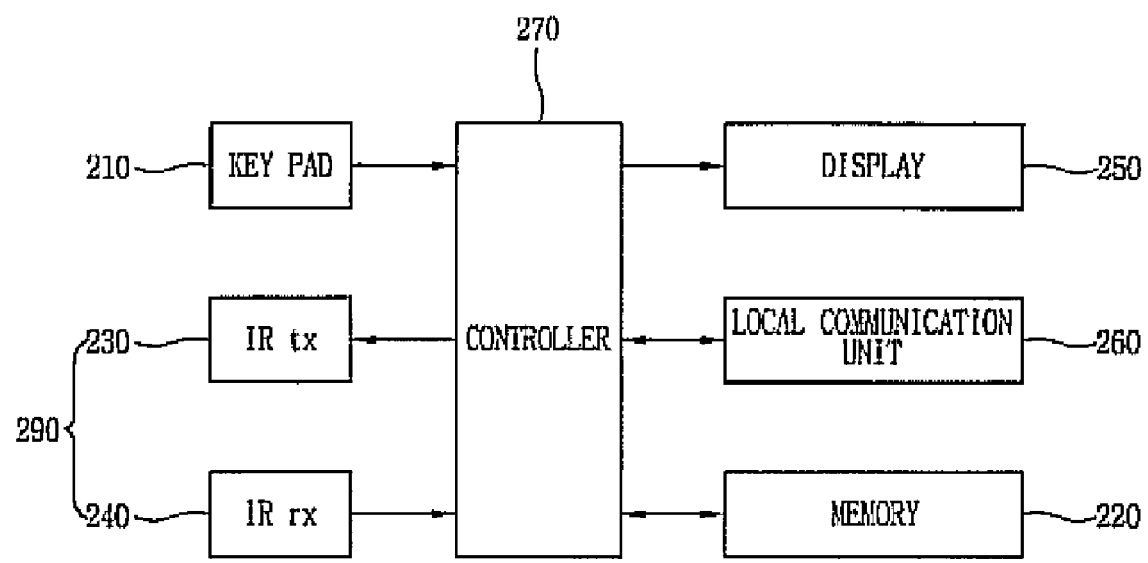
FIG. 9 is a schematic block diagram of the construction of an apparatus according to a third embodiment of the present invention.

FIG. 9 is a schematic block diagram illustrating the construction of a remote controller having a biological information function. A particular functional part can be physically shared by combining the construction of the apparatus of FIG. 5 with the construction of the mobile terminal, to reduce an actually added physical functional part.

The construction also includes functional parts that can be shared as in the mobile terminal in FIG. 7. First, a keypad 210 includes a plurality of number keys and function keys, and outputs key signals with respect to the keys manipulated by a user to a controller 270 of the remote controller. The keypad 210 can, upon manipulation by the user, output key signals for selecting one of a body fat measurement mode for measuring body fat, a pulse measurement mode for measuring pulse and a blood vessel aging degree measurement mode for measuring blood vessel aging degree selected by the user and various biological information inputted by the user and provide it to the controller 270.

A memory 270 can store previously inputted biological information such as age, weight, height, gender and an amount of exercise of the user, or receive the information through the keypad 210 and store it.

An infrared ray transmission unit 230 irradiates infrared rays with a single wavelength of a certain range to a particular portion of the user's body and can have a similar structure to that shown in FIG. 5 or 7. In addition, the remote controller can use the infrared ray transmission unit 230 to provide a control signal to a control target device.

An infrared ray receiving unit 240 can have a similar structure as that shown in FIGS. 5 or 7. Because the infrared ray transmission unit 230 and the infrared ray receiving unit 240 should preferably be arranged to be physically adjacent to each other, they can be integrally comprised as an infrared ray sensor unit 290.

The controller 270 calculates a body fat value and a pulse value based on a signal received through the infrared ray receiving unit 240 and calculates a blood vessel aging degree by using the biological information of the user stored in the memory 220. Besides, the controller 270 also performs a basic control function of the remote controller.

A display unit 250, included in the remote controller, receives display data with respect to key signals inputted from the keypad 210 and displays it under the control of the controller 270, and also displays an operation sate of the electronic device and a plurality of information in the form of icons or characters. This may not be an essential part according to the following.

If the display unit 250 is not provided in the remote controller, a display unit of the control target device which is controlled by the remote controller can be used, which operation is processed by the controller 270. In order to provide such information to the control target device, the infrared ray transmission unit 230 can be used.

If the infrared ray transmission unit 230 is not used for controlling the control target device but the control target device is controlled by using a local area communication unit 260, result information provided by the controller 270 is provided through the local area communication unit 260. The local area communication unit 260 can be a communication unit that supports, for example, IrDA, Bluetooth, ZigBee communication method, etc.

In a different example, the local area communication unit 260 can be added for the purpose of transferring biological information, not for controlling the control target device, and in this case, the biological information (at least one of the calculated body fat value, the pulse value and the blood vessel aging degree value) can be transferred to an arbitrary device having a means for communicating with the local area communication unit 260.

Figure 10:
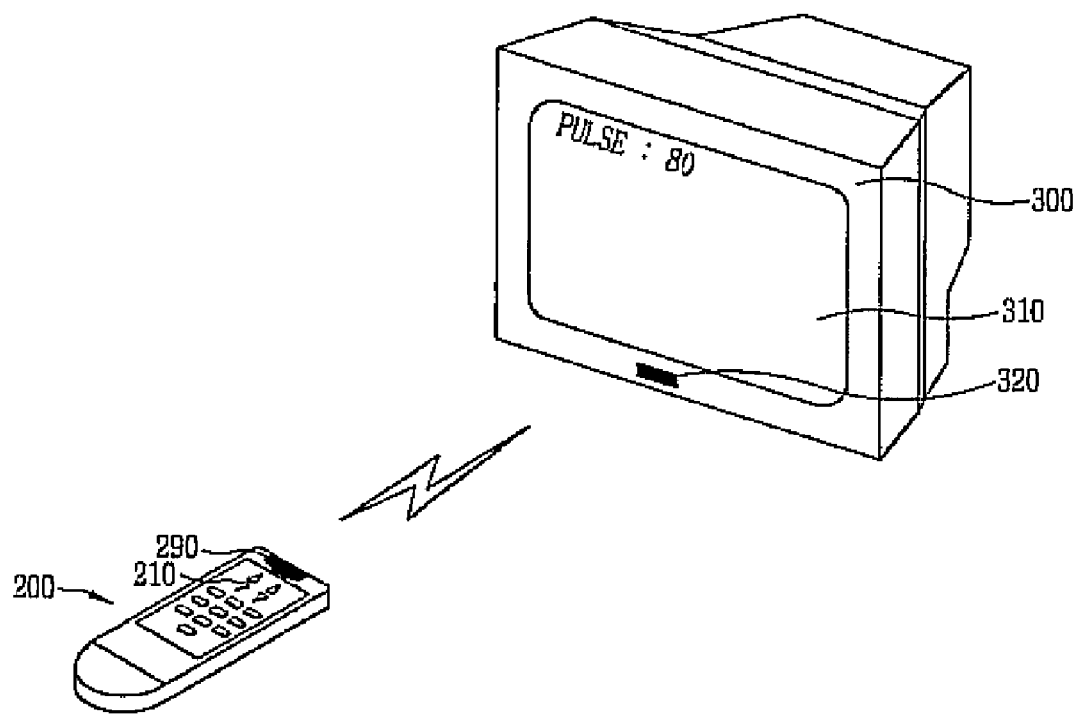
FIG. 10 is an exemplary view of an application of the apparatus of FIG. 9.

FIG. 10 is an exemplary view of an application of the remote controller of FIG. 9, showing an example that a means for measuring biological information is provided in the remote controller 200 having the keypad 210 and the control target device 300 is controlled by using the remote controller 200 through infrared rays.

The remote controller 200 basically includes the keypad 210, the controller and the infrared ray transmission unit. The infrared ray sensor unit 290 can be formed by arranging the infrared ray receiving unit at a position adjacent to the infrared ray transmission unit by using a corresponding functional part, a biological information calculation function can be added to the internal controller, and a memory unit can be added to store the biological information of the user.

In the structure as shown in FIG. 10, the remote controller 200 measures an infrared absorbance of a portion of the measurement target of the user by using the infrared ray sensor unit 290, calculates the body fat value, the pulse value and/or the blood vessel aging degree value based on the measurement information and the user biological information stored in the memory, and transfers the value to the control target device 300 so as to be displayed. The control target device 300 can be an arbitrary device having a display unit or a voice speaking means, and in FIG. 10, a general TV is shown as an example. The TV having the infrared ray receiving unit 320 receives the biological information value provided by the remote controller 20 and displays it on a display region 310. When the control target device is an audio device, the biological information value can be provided as an audio signal to the user.

The remote controller construction as shown in FIG. 10 does not include a local area communication unit, but it will the local area communication unit can be added thereto to be used if desired.

Figure 11A:
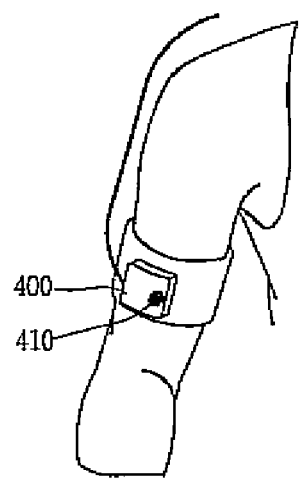
FIGS. 11A to 11C are exemplary views of applications of an apparatus according to a different embodiment.
Figure 11B:
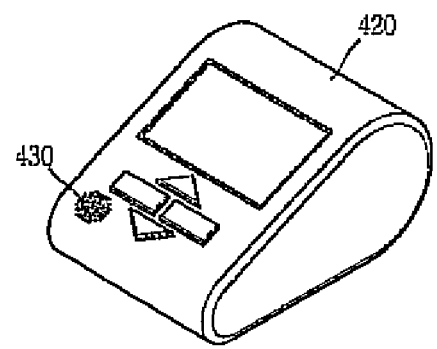
Figure 11C:
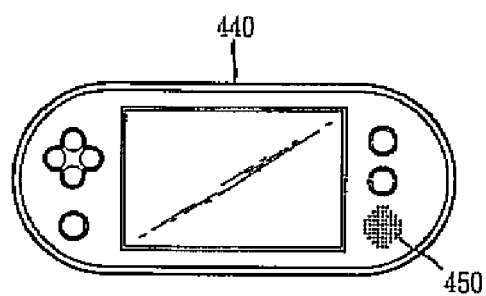

FIGS. 11A to 11C show examples of other devices to which the biological information means can be applied in addition to the already described mobile terminal and the remote controller having the biological information function.

Specifically, FIG. 11A shows a biological information measurement device (an infrared ray sensor unit 410 is formed at a skin attachment portion to be attached on the skin of the user) applied for a mobile audio reproducing device (e.g., an MP3 player, etc.) or a radio set 400, FIG. 11B shows a biological signal measurement device (disposed on a front surface of an infrared ray sensor unit 430) additionally installed at a blood pressure measurement system 420, and FIG. 11C shows a biological signal measurement device (disposed on a front surface of an infrared ray sensor unit 450) additionally installed at a mobile multimedia reproducing device or a game player 440. Among them, the biological signal measurement device applied to the mobile reproducing devices can be constructed to measure the biological signal of the user while using the corresponding device and provide various corresponding services. Also, the biological information measuring apparatus (using the near infrared ray) can be additionally installed at a device for measuring biological information of a different kind such as the blood pressure measurement system to simultaneously measure a plurality of biological information or various biological signals, collectively analyze the result, and provide it.

The structure for improving the precision and efficiency of the biological information measuring apparatus will now be described with various examples.

Figure 12A:
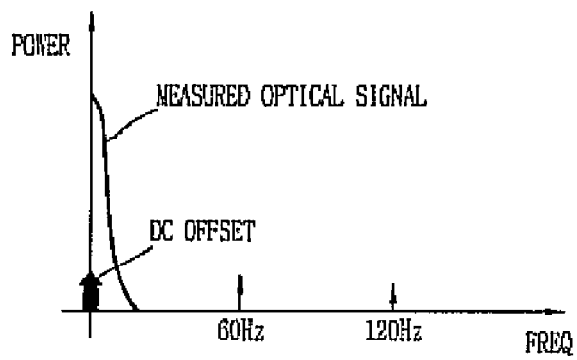
FIGS. 12A to 12C are graphs showing a light measurement signal of each operation unit in the apparatus of FIG. S according to the first embodiment of the present invention.
Figure 12B:
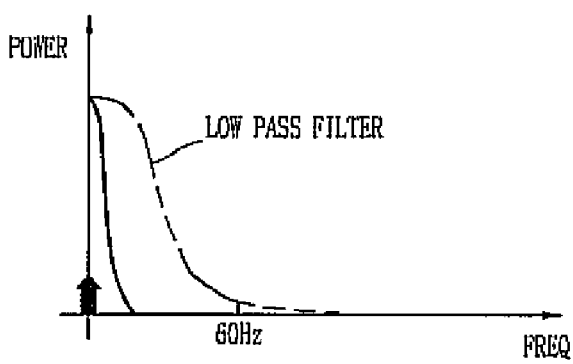
Figure 12C:
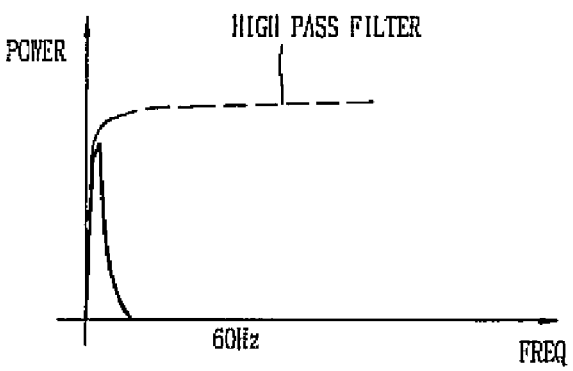

FIGS. 12A to 12C are graphs showing an introduction of various noises generated in the process of measuring the biological information when the biological information measuring apparatus as shown in FIG. 9 is used, namely sequentially showing distortion according to processing of a light reception signal of the infrared ray receiving unit to check the infrared absorbance. Although FIGS. 5, 7 or 9 show merely the schematic block construction for an overall explanation of the overall biological information processing device without mentioning substantial signal processing means, as known, in order for the controller to properly use a signal received from the infrared ray receiving unit, there are basically provided a current/voltage conversion unit for converting a current signal provided by the infrared ray receiving unit into a voltage signal; a low pass filter unit for canceling an RF optical noise (noise caused by a fluorescent lamp) that may be included in the voltage signal obtained through the current/voltage conversion unit; an amplifying unit for amplifying a small signal into a scale that can be handled by the controller; and a high pass filter unit for canceling a DC noise inevitably generated by a power source. The construction order of each element may change, and herein, there is shown noise processing and corresponding signal distortion when a sequential construction is used as described above.

A signal as shown in FIG. 12A is detected by the infrared ray receiving unit and notably contains a DC offset and an RF external lighting noise (especially, noise caused by a fluorescent lamp that flickers at the power main frequency of 60 Hz) in terms of the characteristics of the body information measurement device that uses the DC power.

A signal as shown in FIG. 12B is obtained by low-pass-filtering the signal as shown in FIG. 12A. It is noted that the RF external light noise can be slightly reduced by the low-pass-filtering. In this case, however, because the DC offset value is still contained, an error still occurs in the measurement value. Thus, if the signal is used as it is, the strength of the light signal of the light source should be increased to reduce a rate of the DC offset compared with the measured light signal, which causes an increase in power consumption.

A signal as shown in FIG. 12C is obtained by removing a low frequency DC offset by high-pass-filtering the signal as shown in FIG. 12B. It is noted that the DC offset has been removed. In this case, however, because the signal distortion occurs at the low frequency domain, an error of a measurement value can be generated.

Figure 13:
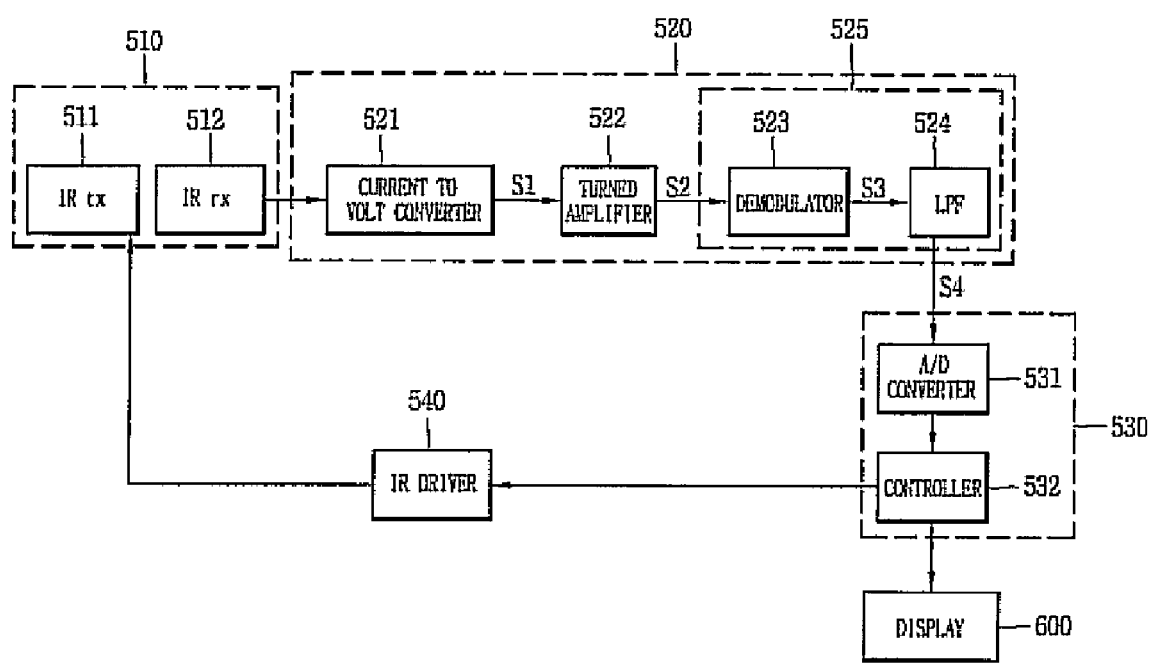
FIG. 13 is a schematic block diagram of the construction of an apparatus according to a fourth embodiment of the present invention.

Accordingly, a light receiving signal processing unit preferably provided between the infrared ray sensor unit and the controller in the apparatus constructions as shown in FIGS. 5, 7 and 9 is formed as shown in FIG. 13 to allow the biological information measuring apparatus to be resistant to noise and perform accurate measurement at a low power consumption.

FIG. 13 shows a partial construction of the biological information measuring apparatus. As shown, the biological information measuring apparatus includes an infrared ray sensor unit 510 for measuring a biological signal; a photodetector driving unit 520 for appropriately filtering and amplifying strength of a detection signal corresponding to light measured and provided to the infrared ray sensor unit 510; a microcontroller 530 for digitizing an output signal provided by the photodetector driving unit 520 and calculating corresponding biological information therefrom; a luminous element driving unit 540 for providing signals for driving a luminous element of the infrared ray sensor unit 510 under the control of the microcontroller 530; and a display 600 for displaying the biological signal measurement result to the user under the control of the microcontroller 530.

The infrared ray sensor unit 10 includes an infrared ray transmitter 511 and an infrared ray receiver 512. Herein, light provided by the infrared ray transmitter 511 is not merely a DC light output but is provided as a light signal modulated according to a particular frequency. For this purpose, the luminous element driving unit 540 connected with the infrared ray transmitter 511 can provide a drive signal based on a particular modulation signal by itself or receive it from a controller 532 within the microcontroller 530 that controls the operation of the luminous element driving unit 540.

The infrared ray transmitter 511 driven by the luminous element driving unit 540 provides a light signal according to a particular modulation frequency, and although the light signal is reflected on a portion of the human body or transmits therethrough, the corresponding frequency can be maintained as it is. The near infrared ray receiver 512 is operated by the photodetector driving unit 520. The photodetector driving unit 520 includes a current-to-voltage converter 521 for converting a change in a current to a change in a voltage; a tuning/amplifying unit 522 for selectively amplifying only the signal portion which has been converted into the voltage; and a matching filter unit 525 for demodulating the tuned/amplified signal based on the modulation signal and removing harmonic content. The matching filter unit 525 includes a demodulator 523 for demodulating the tuned/amplified signal by using the modulation signal used for driving the infrared ray transmitter 511 and a low-pass filter unit 524 for removing a harmonic signal of the signal which has been demodulated by the demodulator 523 by using a low-pass filter. In this case, the modulation signal based on which the modulator 523 performs demodulation is provided by the controller 532 of the microcontroller 530.

The measurement light signal which has been finally obtained after passing through the low-pass filter 524 without noise is provided to the microcontroller 530, and the microcontroller 530 calculates the measurement result according to the biological signal measured by digitizing and internally calculating the signal. An analog/digital converter 531 for digitizing the analog signal can be formed inside or outside the microcontroller 530.

The controller 532 recognizes a signal change in the digitized measurement light and calculates desired biological information (body fat, pulse and blood vessel aging degree) based on the characteristics of the biological information to be measured, and if necessary, the controller may include a digital signal processor for calculating the desired information at a high speed.

In particular, recently, a control function is added to a digital signal processing chip so as to be used like an enhanced microcontroller with a high speed calculation function, or conversely, a means for supporting complicated calculations (e.g., a FIR (Finite Impulse Response) or IIR (Infinite Impulse Response) filter calculation or an FFT(Fast Fourier Transform), etc.) is added to the microcontroller having various supplementary functions to allow the microcontroller to perform digital signal processing, and these days, diverse types of microcontrollers having the function of digital signal processing are mass-produced at a low cost, so a microcontroller having a calculation function with a level desired by a designer can be selected and applied at a reasonable cost to thus provide measurement results of various measurement targets that can be measured through infrared rays.

With the structure as shown in FIG. 13, the DC offset or an external optical noise (60 Hz fluorescent lamp noise or harmonic noise) can be removed without signal distortion, and because the signals are separately measured, although an output of the light source does not have a big size, a signal-to-noise ratio can be maintained to be high and the output of the light source can be lowered, and thus, power consumption can be considerably reduced. The low power consumption contributes to increase portability of the biological signal measuring apparatus, and when the structure is additionally applied to the widely used various types of mobile devices, an increase in power consumption can be suppressed to its maximum level.

FIGS. 14A to 14D are waveform diagrams of a light measurement signal of each functional block in FIG. 13, in which changes due to amplification of the signals have been omitted in order to exhibit signal characteristics of relevance here.

Figure 14A:
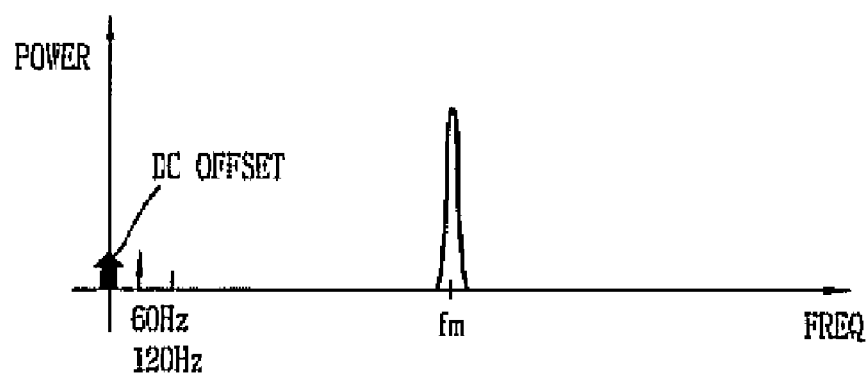
FIGS. 14A to 14D are waveform diagrams of a light measurement signal of each block in the apparatus of FIG. 13.

FIG. 14A shows an output signal (Si) of the current-to-voltage converter 521 of FIG. 13, and it is noted that the measurement light signal includes a DC offset noise and an external light noise (60 Hz and 120 Hz) in addition to the light reception signal which has been modulated to a modulation frequency fm. However, the measured light itself has been modulated to the modulation frequency fm existing at a band (at least 300 Hz or higher band) higher than a band where the noise is generated, so, notably, the measurement signal and the noise are completely separated.

Figure 14B:
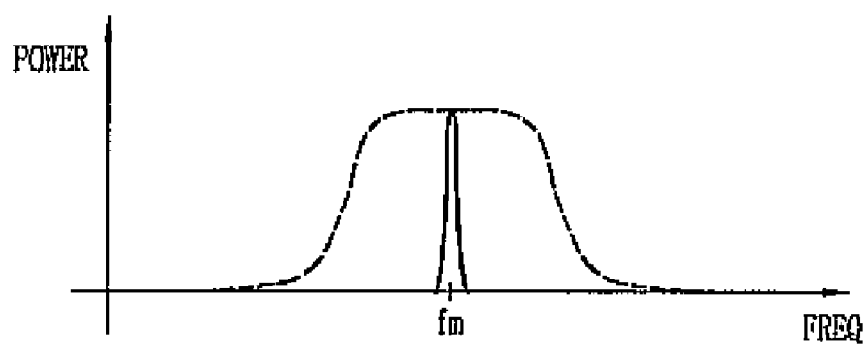

FIG. 14B shows an output signal (S2) of the tuning/amplifying unit 522 of FIG. 13, in which the measurement signal distributed based on the modulation frequency fm was band-pass-filtered and amplified based on the center frequency fm of the corresponding signal. The broken line indicates the pass band portion and the corresponding region exists at a band higher than the DC offset noise and the external light noise (60 Hz and 120 Hz), so it can be noted that various noises have been mostly canceled.

Figure 14C:

FIG. 14C shows an output signal (S3) of the demodulator 523 in FIG. 13, in which the tuned/amplified signal was demodulated by using the modulation signal which was applied for driving the infrared ray transmitter 511. The modulation signal can be fixed one, and preferably, the microcontroller 530 variably generates a proper signal and provides it to the luminous element driving unit 540 and the demodulator 523. The signal measured through the demodulation process is converted into a signal of an actual DC region and harmonics (second harmonics, and actually the higher level harmonics are generated but not shown) are generated at the band (2 fm) which is double the modulation frequency fm.

Figure 14D:

FIG. 14D shows an output signal (S4) of the low pass filter 524 in FIG. 13, in which the harmonic component has been removed from the demodulated signal. The pass band of the low-pass filter 524 can be properly set to be smaller than the modulation frequency fm and filter only a required signal. The broken line indicates a pass band of the low-pass filter 524.

Figure 15:
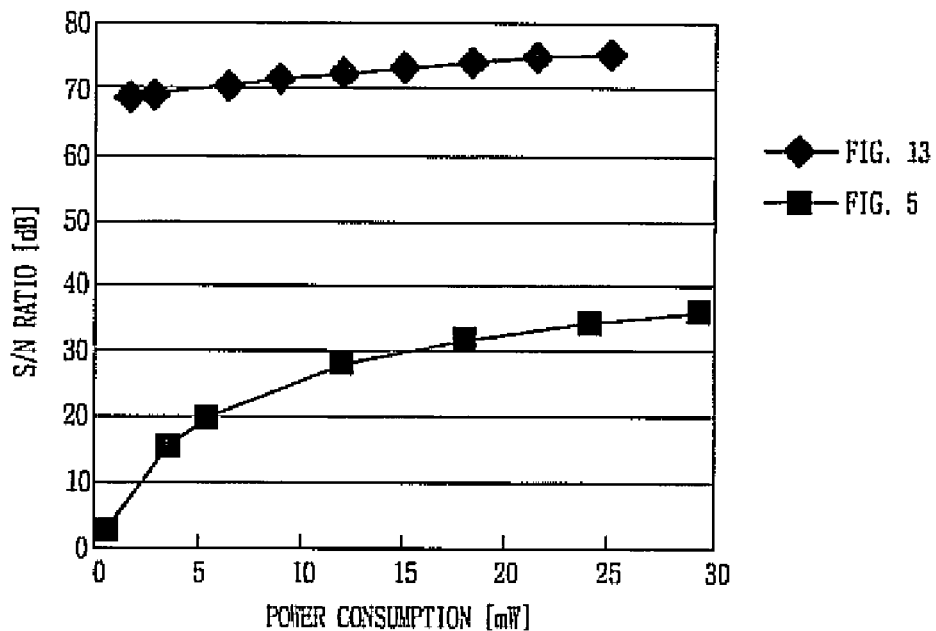
FIG. 15 is a graph plotting power consumption amounts relative to signal-to-noise ratios between the apparatus construction in FIG. 5 and that in FIG. 13.

FIG. 15 is a graph showing an example of comparison of signal-to-noise ratio according to power consumption generated when a light source is driven in a signal processing method operating according to the construction of FIG. 13 and the general construction as shown in FIG. 5. Compared with the related art construction as shown by the rectangle plot, the apparatus according to the construction of FIG. 13 illustrated by the diamond plot shows remarkably improved signal-to-noise ratio characteristics compared with the amount of power consumption.

Figure 16:
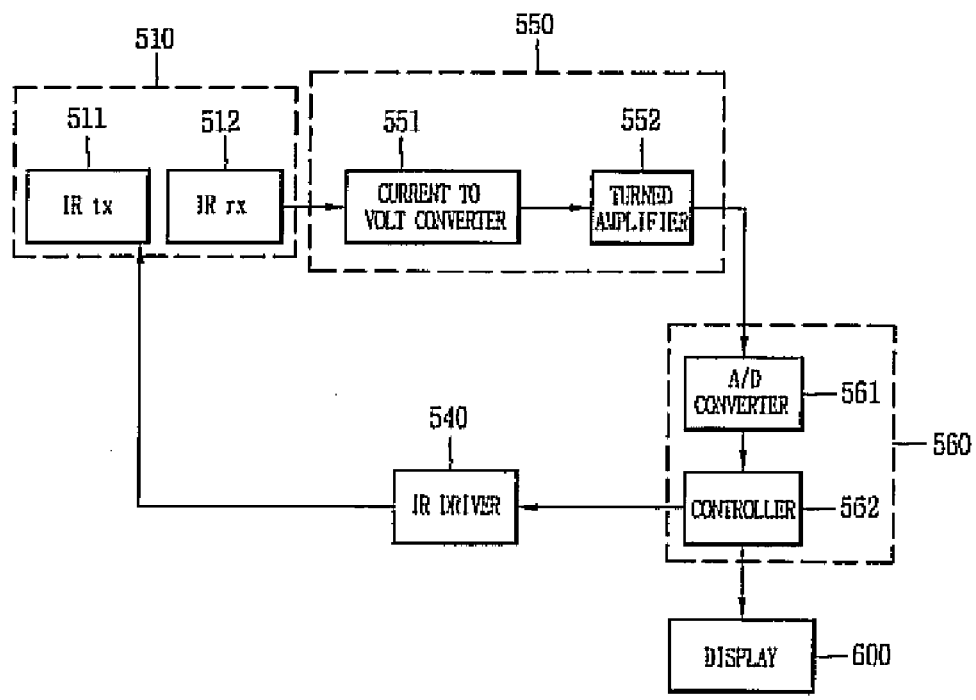
FIG. 16 is a schematic block diagram of the construction of an apparatus according to a fifth embodiment of the present invention.
Figure 17:
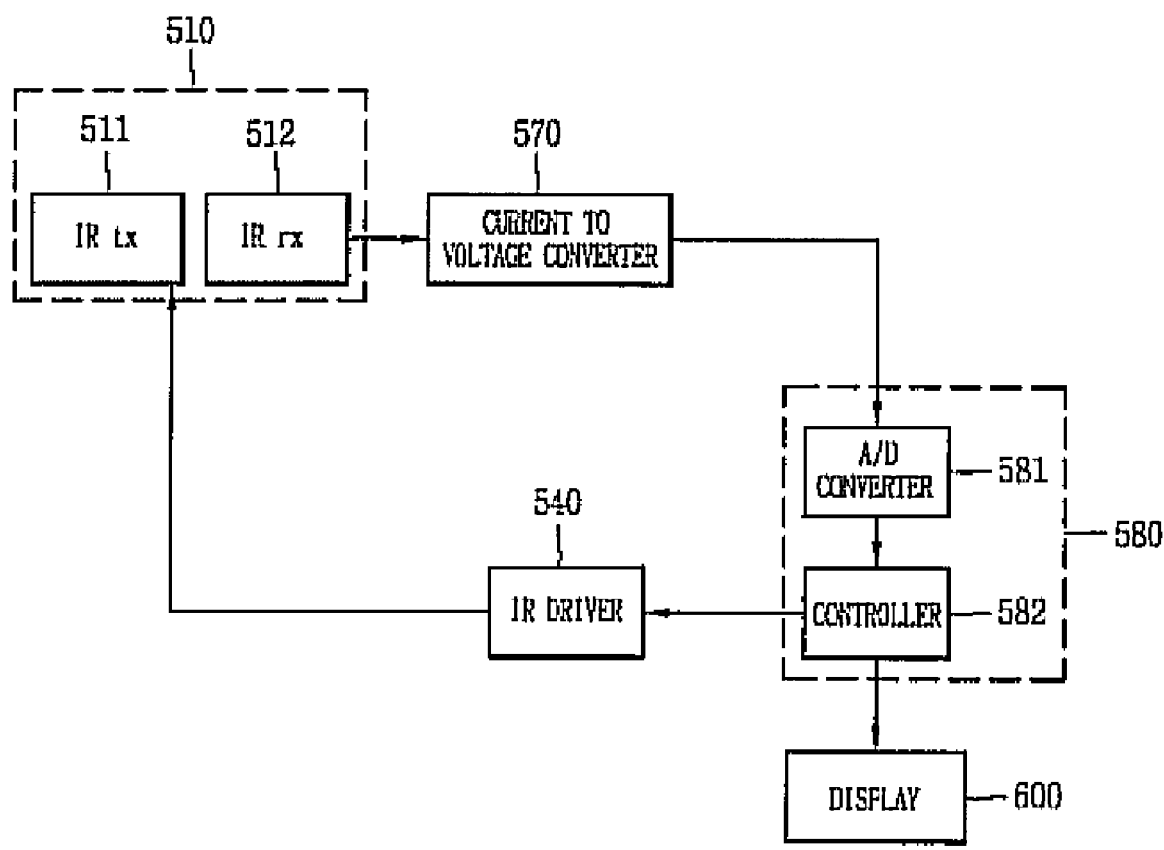
FIG. 17 is a schematic block diagram of the construction of an apparatus according to a sixth embodiment of the present invention.

FIGS. 16 and 17 show a modification of the construction of the apparatus of FIG. 13. FIG. 16 shows the construction of an apparatus wherein the microcontroller can internally perform the function of the matching filter unit of the photodetector driving unit in FIG. 13. In this case, the photodetector driving unit 550 needs only a current-to-voltage converter 551 and a tuning/amplifying unit 552, and a noise-canceled modulation signal provided by the tuning/amplifying unit 552 is directly provided to the microcontroller 560. The microcontroller 560 converts the corresponding signal into a digital signal through an internal analog/digital converter 561 and the corresponding digital signal is processed by a controller 562 that performs the role of the matching filter unit. As the controller 562, a type that is available for digital signal processing as mentioned above can be used or a digital signal processor can be additionally included. The low-pass filter function can be implemented in a digital manner by using the FIR filter or the IIR filter included in the digital signal processor. The function of the demodulator can be implemented through the calculation function of the controller 562.

FIG. 17 shows a case where the controller 562 of a microcontroller 580 integrating the function of the tuning/amplifying unit 552 in the structure of FIG. 16 is used, and the structure excluding the microcontroller 580 is much simplified. In particular, the function of the tuning/amplifying unit is amplifying and filtering signals, so filtering can be performed by using the FIR or the IIR filter included in the digital signal processor and the amplifying function can increase a digital value at a certain ratio, and thus, the controller 582 can maintain a measurement speed based on the conversion speed of the analog/digital conversion unit 581 without much burden.

The configurations as shown in FIGS. 16 and 17 allow the controller to internally perform filtering corresponding to the matching function or the matching and tuning function, so the controller can control the filter characteristics set according to a program if desired. In addition, because a signal can be amplified with a desired gain and the modulation signal can be arbitrarily generated, the matching/tuning characteristics with the modulation signal and the amplifying degree can be optimized by varying various measurement coefficients according to the type of the biological signal to be measured, and accordingly, the precision of measurement can be highly maintained although the type of the biological signal to be measured is changed.

As so far described, the apparatus and method for measuring the biological information according to the present invention have many advantages.

That is, first, the body fat, pulse and the blood vessel aging degree can be measured with a single device by using the infrared rays with a single wavelength of a certain range.

Second, by measuring a plurality of biological information by using infrared rays with the single wavelength, the construction and processing method can be simplified and easily applied to various mobile devices.

Third, because the infrared ray transmission signal and the signal processing method of the infrared ray receiving unit are performed through the modulation and demodulation method and the matching filter is applied for the demodulation, the signal-to-noise ratio can be improved to increase the precision of measurement and the strength of light of the light emitting unit can be reduced to reduce power consumption.

Fourth, at least some of the unit for receiving the modulated infrared ray light and tuning/amplifying it and the unit for matching and filtering the tuned and amplified signal can be implemented in a digital manner through the digital signal processor, whereby the structure of the analog circuitry can be simplified.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalents of such metes and bounds are therefore intended to be embraced by the appended claims.

What is claimed is:

1. An apparatus for measuring biological information comprising:
   an input unit configured to receive an input from a user for selecting each of a body fat measurement mode, a pulse measurement mode and a blood vessel aging degree measurement mode;
   a memory configured to store biological information of the user;
   an infrared ray transmission and reception unit configured to radiate infrared rays having a single wavelength, and measure an infrared absorbance of a certain portion of the user's body by analyzing a reflected amount of the radiated infrared rays;
   a controller configured to calculate each one of a body fat value, a pulse value and a blood vessel aging degree value based on the measured infrared absorbance and stored biological information according to the measurement mode selected via the input unit;
   a current/voltage conversion unit configured to convert a current signal provided by the infrared ray transmission and reception unit into a voltage signal;
   a low pass filter unit configured to filter the voltage signal to cancel radio frequency (RF) optical noise included in the voltage signal;
   an amplifying unit configured to amplify the filtered voltage signal;
   a high pass filter configured to filter direct current (DC) noise generated by a power source; and
   a display unit configured to display at least one of the calculated body fat value, pulse value and blood vessel aging degree value,
   wherein the single wavelength is the same in the body fat measurement mode, the pulse measurement mode and the blood vessel aging degree measurement mode.

2. The apparatus of claim 1, wherein the infrared ray transmission and reception unit comprises at least one infrared light emitting diode and one of at least one infrared sensitive photodiode and an infrared sensitive photo-transistor.

3. The apparatus of claim 1, wherein when the body fat measurement mode is selected, the controller calculates the body fat value by using the measured infrared absorbance and at least one of weight, height, gender and an amount of exercise of the user corresponding to the biological information.

4. The apparatus of claim 1, wherein when the pulse measurement mode is selected, the controller calculates the pulse value by analyzing a change of the infrared absorbance measurement value.

5. The apparatus of claim 1, wherein when the blood vessel aging degree measurement mode is selected, the controller calculates the blood vessel aging degree value by differentiating a signal change of the infrared absorbance measurement value by a certain number of times and analyzing the size and form of peaks of the differentiated signal.

6. The apparatus of claim 1, further comprising:
a transmission driving unit connected with the infrared ray transmission and reception unit and configured to provide a drive signal for transmission based on a particular modulation wavelength; and
a reception driving unit connected with the infrared ray transmission and reception unit configured to tune/demodulate a received signal and provide the processed signal to the controller.

7. A method for measuring biological information, the method comprising:
receiving an input for selecting each of a body fat measurement mode, a pulse measurement mode and a blood vessel aging degree measurement mode;
radiating infrared rays having a single wavelength to a particular portion of a user's body, and measuring an infrared absorbance of the user's body by analyzing a reflected amount of the radiated infrared rays;
calculating each of a body fat value, a pulse value and a blood vessel aging degree value based on the measured infrared absorbance and pre-set user biological information according to the selected measurement mode;
detecting and converting a current signal generated by the radiated infrared rays into a voltage signal;
filtering radio frequency (RF) optical noise included in the voltage signal by low-pass-filtering;
amplifying the filtered voltage signal;
filtering direct current (DC) noise generated by a power source by high-pass-filtering; and
displaying at least one of the calculated body fat value, the pulse value and the blood vessel aging degree value,
wherein the single wavelength is the same in the body fat measurement mode, the pulse measurement mode and the blood vessel aging degree measurement mode.

8. The method of claim 7, wherein, in the calculating step, when the body fat measurement mode is selected, a body fat value is calculated by using the measured infrared absorbance and at least one of weight, height, gender and an amount of exercise of the user corresponding to the biological information.

9. The method of claim 7, wherein, in the calculating step, when the pulse measurement mode is selected, a pulse value is calculated by analyzing a change of the infrared absorbance measurement value.

10. The method of claim 7, wherein, in the calculating step, when the blood vessel aging degree measurement mode is selected, the blood vessel aging degree value is calculated by differentiating a signal change of the infrared absorbance measurement value by a certain number of times and analyzing sizes and forms of peaks of the differentiated signal.

11. The method of claim 7, wherein the measuring the infrared absorbance comprises:
modulating the infrared rays with a modulation signal and radiating the infrared rays;
receiving an amount of reflection of the radiated infrared rays as an electrical signal; and
demodulating the received electrical signal based on the modulation signal.

12. A mobile terminal comprising:
a keypad configured to receive an input from a user for selecting each of a body fat measurement mode, a pulse measurement mode and a blood vessel aging degree measurement mode;
a memory configured to store biological information of the user;
an infrared ray transmission and reception unit configured to radiate infrared rays having a single wavelength, and measure an infrared absorbance of a certain portion of the user's body by analyzing an amount of infrared rays reflected therefrom;
a controller configured to calculate each of a body fat value, a pulse value and a blood vessel aging degree value based on the measured infrared absorbance and biological information according to the measurement mode selected by the user;
a voice conversion unit configured to convert at least one of the calculated body fat value, the pulse value and the blood vessel aging degree value into a voice signal and outputting the voice signal; and
a display unit configured to display at least one of the calculated body fat value, the pulse value and the blood vessel aging degree value,
wherein the single wavelength is the same in the body fat measurement mode, the pulse measurement mode and the blood vessel aging degree measurement mode.

13. A remote controller, comprising:
a keypad configured to receive an input from a user for selecting each of a body fat measurement mode, a pulse measurement mode and a blood vessel aging degree measurement mode;
a memory configured to store biological information of the user;
an infrared ray transmission and reception unit configured to radiate infrared rays having a single wavelength, and measure an infrared absorbance value of a certain portion of the user's body by analyzing an amount of the radiated infrared rays reflected therefrom;
a microcomputer configured to calculate each of a body fat value, a pulse value and a blood vessel aging degree value based on the measured infrared absorbance value and biological information according to the measurement mode selected by the user;
a local area communication unit configured to transmit at least one of the calculated body fat value, the pulse value and the blood vessel aging degree value to an external electronic device having a display unit,
wherein the single wavelength is the same in the body fat measurement mode, the pulse measurement mode and the blood vessel aging degree measurement mode.

14. The remote controller of claim 13, wherein the local area communication unit comprises at least one of an infrared data association (IrDA) device, a Bluetooth device and a ZigBee device.

15. The apparatus of claim 1, wherein the single wavelength is in a range of 700 nm to 1,000 nm.

16. The method of claim 7, wherein the single wavelength is in a range of 700 nm to 1,000 nm.

17. The mobile terminal of claim 12, wherein the single wavelength is in a range of 700 nm to 1,000 nm.

18. The remote controller of claim 13, wherein the single wavelength is in a range of 700 nm to 1,000 nm.

19. The apparatus of claim 1, wherein the apparatus is integrated into a portable device comprising a mobile terminal, a remote controller, a mobile audio reproducing device, a mobile multimedia reproducing device, or a game player.

20. The method of claim 7, wherein the method is executed by a portable device comprising a mobile terminal, a remote controller, a mobile audio reproducing device, a mobile multimedia reproducing device, or a game player.

21. The remote controller of claim 13, wherein the at least one of the calculated body fat value, pulse value or blood vessel aging degree value is output via an external control target device that is controlled by the remote controller, the control target device having a displaying or voice speaking means.

22. The apparatus of claim 1, wherein the measurement mode is selected from a group consisting of a body fat measurement mode, a pulse measurement mode and a blood vessel aging degree measurement mode.

23. The method of claim 7, wherein the measurement mode is selected from a group consisting of a body fat measurement mode, a pulse measurement mode and a blood vessel aging degree measurement mode.

24. The mobile terminal of claim 12, wherein the measurement mode is selected from a group consisting of a body fat measurement mode, a pulse measurement mode and a blood vessel aging degree measurement mode.

25. The remote controller of claim 13, wherein the measurement mode is selected from a group consisting of a body fat measurement mode, a pulse measurement mode and a blood vessel aging degree measurement mode.

* * * * *